(12) United States Patent
Beier et al.

(10) Patent No.: US 6,680,388 B2
(45) Date of Patent: Jan. 20, 2004

(54) METHOD FOR PREPARING SUBSTITUTED 5-AMINO-N-PHENYL-1,2,4-TRIAZOLE-3-SULFONAMIDES

(75) Inventors: Christian Beier, Wuppertal (DE); Reinhard Lantzsch, Wuppertal (DE)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 10/311,038

(22) PCT Filed: Jun. 5, 2001

(86) PCT No.: PCT/EP01/06386

§ 371 (c)(1),
(2), (4) Date: Dec. 12, 2002

(87) PCT Pub. No.: WO01/96316

PCT Pub. Date: Dec. 20, 2001

(65) Prior Publication Data

US 2003/0162975 A1 Aug. 28, 2003

(30) Foreign Application Priority Data

Jun. 16, 2000 (DE) .......................... 100 29 878
Aug. 4, 2000 (DE) .......................... 100 38 020

(51) Int. Cl.[7] .............................................. C07D 249/14
(52) U.S. Cl. .................................................. 548/263.8
(58) Field of Search ...................................... 548/263.8

(56) References Cited

U.S. PATENT DOCUMENTS

| | | | |
|---|---|---|---|
| 4,734,123 A | 3/1988 | Monte | 71/92 |
| 4,740,233 A | 4/1988 | Kleschick et al. | 71/92 |
| 4,741,764 A | 5/1988 | Kleschick et al. | 71/92 |
| 4,755,212 A | 7/1988 | Kleschick et al. | 71/92 |
| 4,818,273 A | 4/1989 | Kleschick et al. | 71/90 |
| 4,886,883 A | 12/1989 | Kleschick et al. | 544/263 |
| 4,937,350 A | 6/1990 | Shankar et al. | 548/263.8 |
| 4,954,163 A | 9/1990 | Kleschick et al. | 71/92 |
| 4,983,772 A | 1/1991 | Kleschick et al. | 564/442 |
| 4,988,812 A | 1/1991 | Kim et al. | 544/263 |
| 5,013,351 A | 5/1991 | Jelich et al. | 71/92 |

FOREIGN PATENT DOCUMENTS

| | | |
|---|---|---|
| EP | 0 246 749 | 11/1987 |
| EP | 0 375 061 | 6/1990 |
| GB | 951652 | 3/1964 |

OTHER PUBLICATIONS

Sankar R. B. et al: "Synthesis of 1,2,4–Triazoloi, 5–Apyrimidine–2–Sulfonamides" Journal of Heterocyclic Chemistry, Hetero Corp., Tampa, FL, US, Bd. 30, Nr. 1, Jan. 1993, Seiten 169–172, XP000943000 ISSN: 0022–152X in der Anmeldung erwähnt Scheme 2 Seite 170; Beispiel 6.

*Primary Examiner*—Patricia L. Morris
(74) *Attorney, Agent, or Firm*—Richard E. L. Henderson

(57) ABSTRACT

The present invention relates to a process for preparing 5-amino-N-phenyl-1,2,4-triazole-3-sulfonamides of the formula (I)

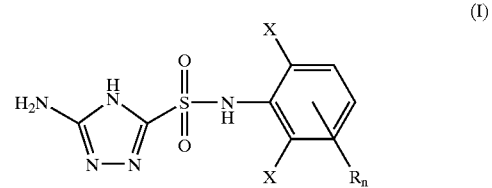

(I)

where
 X is halogen, cyano or nitro,
 R is hydrogen or optionally halogen-substituted $C_1$–$C_4$-alkyl, and
 n is 1 or 2,
by reacting 5-amino-3-chlorosulfonyl-1,2,4-triazole of the formula (II)

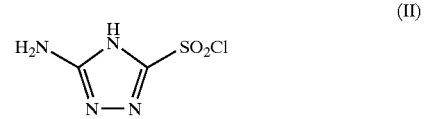

(II)

with substituted anilines of the formula (III)

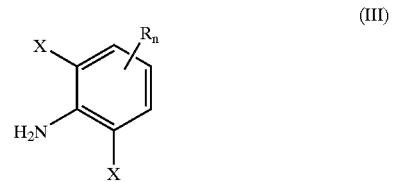

(III)

where X, n and R are as defined for formula (I), in the absence of a solvent.

18 Claims, No Drawings

METHOD FOR PREPARING SUBSTITUTED 5-AMINO-N-PHENYL-1,2,4-TRIAZOLE-3-SULFONAMIDES

The invention relates to a novel process for preparing 5-amino-N-phenyl-1,2,4-triazole-3-sulfonamides, which are familiar as intermediates for active ingredients in agriculture, in particular for substituted, herbicidally active 1,2,4-triazolo[1,5-a]pyrimidine-2-sulfonamides.

It is known that triazolopyrimidinesulfonamides may be prepared by reacting triazole pyrimidine sulfonyl chlorides with alkylamines or aniline (GB-A 951 652, EP-A 0 142 152, DE-A 36 40 155, U.S. Pat. No. 4,740,233). However, in these processes, the amine first has to be partially activated by metallation using n-butyllithium or alkali metal hydrides. The preparation of triazolopyrimidinesulfonamides having a substitution pattern desirable for herbicidal effectiveness by a multistage reaction from other triazolopyrimidinesulfonamides comprising oxidative cleavage of the pyrimidine ring and subsequent ring reclosure (U.S. Pat. No. 4,734,123; J. Heterocyclic Chem., 30, 169 (1993)) or from other triazolopyrimidinesulfonamides in a multistep reaction by intermediate conversion to trialkylsilyl derivatives (U.S. Pat. No. 4,910,306) has also been described. The use of organometallic compounds and also losses in introducing and cleaving protecting groups and in the transformations are disadvantageous in these synthetic routes to the herbicidally active triazolopyrimidinesulfonamides.

The preparation of the triazolopyrimidinesulfonamides by another route with high yield and efficiency is accordingly desirable.

To this end, it has been suggested that triazolopyrimidinesulfonamides could be prepared from 5-amino-1,2,4-triazole-3-sulfonamides which have previously been obtained by reacting an appropriate chlorosulfonyltriazole with a substituted aniline derivative (EP-A 0 375 061). However, it was found that the preparation of the compound 5-amino-N-(2,6-dichloro-3-methylphenyl)-1,2,4-triazole-3-sulfonamide from the reaction of 2,6-dichloro-3-methylaniline with 5-amino-3-chlorosulfonyl-1,2,4-triazole in the presence of an organic solvent only leads to a yield of 67% after an extremely long reaction time of 5 days. Likewise, the same reaction step when acetic acid is used as solvent also only gives a 67% yield after 5.5 hours of reaction time.

Further known processes for preparing 5-amino-N-phenyl-1,2,4-triazole-3-triazolesulfonamides are likewise not completely satisfactory with regard to the achievable yields (EP-A 0 246 749).

According to the invention, it has been found that the substituted 5-amino-1,2,4-triazole-3-sulfonamides required for preparing triazolopyrimidinesulfonamides surprisingly succeeds by reacting the appropriate slow-reacting, dihalogenated aniline derivatives with the appropriate chlorosulfonyltriazole derivatives in very good yields with negligible formation of by-products when the reaction is carried out as an aniline melt even without addition of an auxiliary base and in the absence of a solvent at a short reaction time of from 30 minutes to 6 hours. In the process according to the invention, both the reaction product and the unconverted aniline may be particularly efficiently isolated in high purity.

It has accordingly been found that substituted 5-amino-N-phenyl-1,2,4-triazole-3-sulfonamides of the general formula (I)

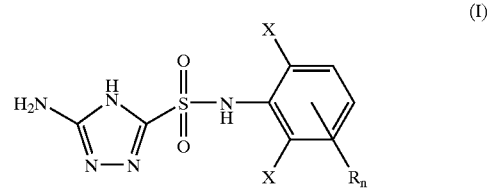

where
X is halogen (in particular fluorine, chlorine or bromine), cyano or nitro,
R is hydrogen or optionally halogen-substituted $C_1$–$C_4$-alkyl, and
n is 1 or 2,
are obtained in very good yields and in high purity on reacting 5-amino-3-chlorosulfonyl-1,2,4-triazole of the formula (II)

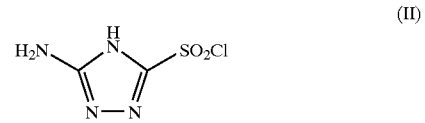

with a substituted aniline of the general formula (III)

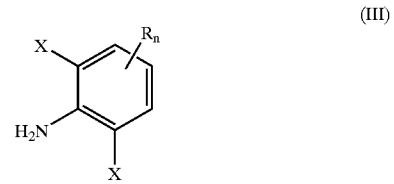

where
X, n and R are as defined above,
in the absence of a solvent.

In formula (I), X is preferably fluorine, chlorine or bromine.

The process according to the invention is particularly advantageous for preparing 5-amino-N-(2,6-dichloro-3-methylphenyl)-1,2,4-triazole-3-sulfonamide of the formula (Ia)

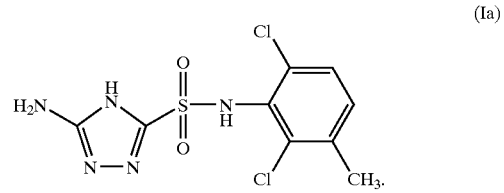

In this case, the product is obtained by reacting 5-amino-3-chlorosulfonyl-1,2,4-triazole of the formula (II)

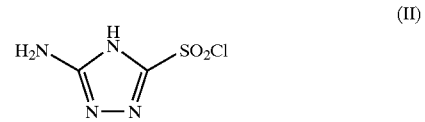

with 2,6-dichloro-3-methylaniline of the formula (IIIa)

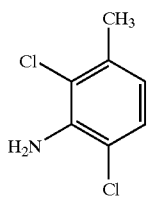

(IIIa)

in the absence of a solvent according to the invention.

In the process according to the invention, it is also generally unnecessary to add an auxiliary base (for example, potassium carbonate).

The direct reaction in the melt and not using the solvent described in the exemplary examples of EP-A 0 375 061 surprisingly provides a novel process which allows the preparation of 5-amino-N-phenyl-1,2,4-triazole-3-sulfonamides in very good yields and in high purity after a short reaction time.

Carrying out the reaction of the process according to the invention in the absence of a solvent provides the further advantage of avoiding the otherwise necessary, complicated recovery of the organic solvent after carrying out the reaction. Since no auxiliary base is required either, no waste products are formed. A substantial advance of the process according to the invention is the short reaction time. Even after 30 minutes to 6 hours, virtually quantitative yields are achieved.

Finally, the process according to the invention is notable in that only gaseous HCl is by-produced, which is easy to bind. The excess aniline can be simply removed by extraction and can accordingly be efficiently recovered.

A preferred embodiment of the process according to the invention is accordingly the variant which involves extracting the excess aniline in a further reaction step after the reaction of the starting materials using a water-immiscible organic solvent and then isolating it. This achieves quantitative recovery of excess aniline in high purity in a simple manner.

In a further preferred embodiment, the reaction product of the reaction is isolated by precipitating out of an aqueous solution using a salt-forming acid, preferably HCl, and subsequent filtration.

The process according to the invention accordingly provides an enrichment of the prior art, since it allows very advantageous preparation of 5-amino-N-phenyl-1,2,4-triazole-3-sulfonamides. This eases access to the herbicidal 1,2,4-triazolo[1,5-a]pyrimidine-2-sulfonamides based on these intermediates.

The 5-amino-3-chlorosulfonyl-1,2,4-triazole of the formula (II) to be used as the starting compound in the process according to the invention and also the substituted anilines of the formula (III) and the 2,6-dichloro-3-methylaniline of the formula (IIIa) are already known and may be prepared by known processes (cf., for example, EP-A 0 375 061).

The reaction according to the invention of the substituted anilines with 5-amino-3-chlorosulfonyl-1,2,4-triazole is generally carried out at temperatures of from 90° C. to 150° C., preferably from 115° C. to 145° C.

The reaction according to the invention of the substituted anilines with 5-amino-3-chlorosulfonyl-1,2,4-triazole is generally carried out for reaction times of from 30 minutes to 6 hours, preferably from 30 to 120 minutes.

To carry out the process according to the invention, preference is given to using the aniline in excess for preparing the compounds of the formula (I). In general, from 1.2 to 10 moles, preferably from 1.5 to 5 moles, of the aniline of the formula (III) are used per mole of 5-amino-3-chlorosulfonyl-1,2,4-triazole of the formula (II).

The above-described, preferred embodiment of the process according to the invention involves admixing the reaction mixture after the end of the reaction with an aqueous basic solution (preferably aqueous sodium hydroxide) and shaking it with a virtually water-immiscible organic solvent, for example, dichloromethane or toluene, washing the organic phase with water, drying it, and isolating the unconverted aniline of the formula (III) used as the starting material after evaporating off this solvent.

The compounds of the formula (I) can be worked up and isolated in a customary manner. Preference is given to admixing the reaction mixture after the end of the reaction with an aqueous basic solution (preferably aqueous sodium hydroxide) and shaking it with a virtually water-immiscible organic solvent, such as dichloromethane, to obtain an aqueous phase comprising the product. The end product of the formula (I) may also be extracted from the aqueous phase after acidification with a virtually water-immiscible organic solvent, for example ethyl acetate, and isolated after distilling off the solvent. However, preference is given to admixing the aqueous phase obtained with a salt-forming acid (for example, HCl). The end product of the formula (I) which precipitates may in this case be obtained after filtration as the residue and, if desired, further purified in a customary manner.

In this preferred embodiment of the process, the precipitating reagent used is preferably a hydrochloric acid solution (concentration: one normal to concentrated) and the precipitation is carried out in the acid range of from pH 0 to 6, preferably pH 0–3.

In a further variant according to the invention of the process, the compound 5-amino-3-chlorosulfonyl-1,2,4-triazole of the formula (II) is added in portions or continuously to the aniline of the formula (III).

In this preferred variant, the triazole is added in portions or continuously to the aniline over a period of at least 10 minutes, preferably at least 30 minutes. Addition over a period of from 10 minutes to 2 hours is regarded as particularly advantageous.

The process according to the invention may also be carried out in such a manner that the triazole of the formula (II) is completely continuously reacted with aniline, i.e. the reactants are continuously introduced into the reaction chamber and the reaction product is continuously removed. Preference is given to using the aniline in excess. Useful reaction chambers include in particular tubular or loop reactors.

PREPARATIVE EXAMPLES

Example 1

In a 250 ml three-necked flask equipped with an internal thermometer, reflux condenser and mechanical stirrer, 66 g (0.375 mol) of 2,6-dichloro-3-methylaniline are heated under argon by an oil bath preheated to 130° C. to an internal temperature of about 120–130° C. 27.3 g (0.15 mol) of 5-amino-3-chlorosulfonyl-1,2,4-triazole are added to the stirred melt and the mixture is stirred vigorously. After 30 minutes, no more sulfochloride can be detected by HPLC, but instead only 5-amino-N-(2,6-dichloro-3-methylphenyl)-1,2,4-triazole-3-sulfonamide and also 2,6-dichloro-3-methylaniline. The reaction mixture is cooled and admixed slowly with 45% aqueous sodium hydroxide solution with stirring to about pH 12. The alkaline solution is stirred for 1 hour and then extracted 3 times with 200 ml of dichloromethane each time, in order to remove excess aniline. The removed, united organic phases are dried over sodium sulfate and filtered, and the solvent is removed under reduced pressure. 43.8 g of 2,6-dichloro-3-methylaniline (purity>99%, HPLC/UV percentage area) are obtained. The extracted aqueous phase is acidified using 32% HCl to about pH 1 and stirred for 1 hour. The precipitated solid is filtered off with suction, washed with cold water and is dried overnight under reduced pressure. 40.0 g of 5-amino-N-(2,6-dichloro-3-methylphenyl)-1,2,4-triazole-3-sulfonamide are obtained in a purity of 98.7% (HPLC/UV percentage area) as a colorless solid having a melting point of 240–241° C. The theoretical yield is found to be 82.7%, and based on unrecovered aniline the yield is 98.4% of theory.

Example 2

4.4 g (0.025 mol) of 2,6-dichloro-3-methylaniline are heated to 110° C., 1.8 g (0.01 mol) of 5-amino-3-chlorosulfonyl-1,2,4-triazole are added under argon and the suspension is stirred for 90 minutes at this temperature. After work-up similar to example 1, 3.1 g (99.4% purity) of 2,6-dichloro-3-methylaniline and 1.81 g (95.3% purity) of 5-amino-N-(2,6-dichloro-3-methylphenyl)-1,2,4-triazole-3-sulfonamide are obtained. The theoretical yield is found to be 56.2%, and based on unrecovered aniline the yield is 76.1% of the theory.

Example 3

4.4 g (0.025 mol) of 2,6-dichloro-3-methylaniline are heated to 110° C., 1.8 g (0.01 mol) of 5-amino-3-chlorosulfonyl-1,2,4-triazole are added under argon and the suspension is stirred for 6 hours at this temperature. After work-up similar to example 1, 2.9 g (99.3% purity) of 2,6-dichloro-3-methylaniline and 2.21 g (96.1% purity) of 5-amino-N-(2,6-dichloro-3-methylphenyl)-1,2,4-triazole-3-sulfonamide are obtained. The theoretical yield is found to be 68.6%, and based on unrecovered aniline the yield is 80.5% of the theory.

Example 4

Comparative Example According to EP 0 375 061

3.65 g (0.02 mol) of 5-amino-3-chlorosulfonyl-1,2,4-triazole and 3.5 g (0.02 mol) of 2,6-dichloro-3-methylaniline are suspended in 40 ml of acetonitrile under argon and stirred at reflux temperature for 16 h. After cooling, the precipitate is filtered off with suction and dried. 2.0 g (99.4% purity) of 2,6-dichloro-3-methylaniline are obtained. The filtrate is admixed with water and extracted 3 times with dichloromethane. The aqueous phase is acidified using 32% hydrochloric acid to pH 1, the precipitated solid is filtered off with suction and dried under reduced pressure. 0.775 g (96.9% purity) of 5-amino-N-(2,6-dichloro-3-methylphenyl)-1,2,4-triazole-3-sulfonamide is obtained. The theoretical yield is found to be 12%, and based on unrecovered aniline the yield is 28% of theory.

Example 5

Comparative Example According to EP 0 375 061

0.9 g (0.005 mol) of 5-amino-3-chlorosulfonyl-1,2,4-triazole, 0.9 g (0.005 mol) of 2,6-dichloro-3-methylaniline and 0.7 g (0.005 mmol) of dried potassium carbonate are suspended in 40 ml of dry acetonitrile under argon and stirred at reflux temperature for 16 h. After cooling, the precipitate is filtered off with suction and dried. 0.8 g (88.9%, 94.1% purity) of 2,6-dichloro-3-methylaniline is obtained. In the filtrate, only the sulfonic acid as hydrolysis product of the sulfochloride used can be detected by HPLC.

Example 6

9.1 g (0.05 mol) of 5-amino-3-chlorosulfonyl-1,2,4-triazole (83.7% purity) are added in portions under argon over 1 hour to a melt of 22 g (0.125 mol) of 2,6-dichloro-3-methylaniline heated to 120° C. and stirred, and the suspension is stirred for 90 minutes at this temperature. After a similar work-up to example 1, 14.8 g (99.0% purity) of 2,6-dichloro-3-methylaniline and 13.5 g (90.8% purity) of 5-amino-N-(2,6-dichloro-3-methylphenyl)-1,2,4-triazole-3-sulfonamide are obtained. The theoretical yield is found to be 90.9%, and based on unrecovered aniline the yield is 98.1% of theory.

What is claimed is:

1. A process for preparing a substituted 5-amino-N-phenyl-1,2,4-triazole-3-sulfonamide of the formula (I)

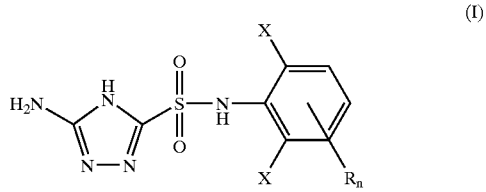

where

X is halogen, cyano, or nitro,

R is hydrogen or optionally halogen-substituted $C_1$–$C_4$-alkyl, and n is 1 or 2, comprising reacting 5-amino-3-chlorosulfonyl-1,2,4-triazole of the formula (II)

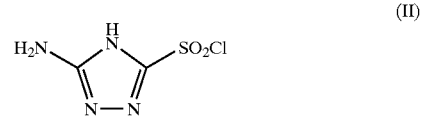

with a substituted aniline of the formula (III)

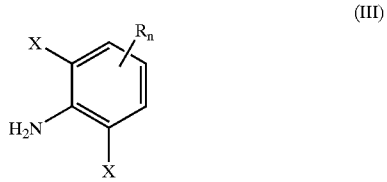

where X, n, and R are as defined for formula (I), in the absence of a solvent.

2. A process for preparing 5-amino-N-(2,6-dichloro-3-methylphenyl)-1,2,4-triazole-3-sulfonamide of the formula (Ia)

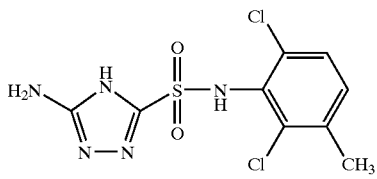

comprising reacting 5-amino-3-chlorosulfonyl-1,2,4-triazole of the formula (II)

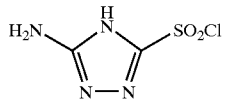

with 2,6-dichloro-3-methylaniline of the formula (III)

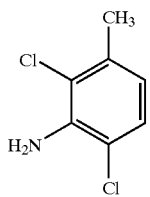

in the absence of a solvent.

3. The process according to claim 1 wherein the reaction is carried out without adding an auxiliary base.

4. The process according to claim 2 wherein the reaction is carried out without adding an auxiliary base.

5. The process according to claim 1 carried out at temperatures of from 90° C. to 150° C.

6. The process according to claim 2 carried out at temperatures of from 90° C. to 150° C.

7. The process according to claim 1 carried out at temperatures of from 115° C. to 145° C.

8. The process according to claim 2 carried out at temperatures of from 115° C. to 145° C.

9. The process according to claim 1 wherein the reaction is carried out for from 30 minutes to 6 hours.

10. The process according to claim 2 wherein the reaction is carried out for from 30 minutes to 6 hours.

11. The process according to claim 1 wherein from 1.2 to 10 moles of the aniline of the formula (III) are used in the reaction per mole of 5-amino-3-chloro-sulfonyl-1,2,4-triazole of the formula (II).

12. The process according to claim 2 wherein from 1.2 to 10 moles of 2,6-dichloro-3-methylaniline of the formula (III) are used in the reaction per mole of 5-amino-3-chlorosulfonyl-1,2,4-triazole of the formula (II).

13. The process according to claim 1 wherein any excess aniline is extracted after the reaction in a further reaction step by extraction with a water-immiscible organic solvent and then isolated.

14. The process according to claim 2 wherein any excess aniline is extracted after the reaction in a further reaction step by extraction with a water-immiscible organic solvent and then isolated.

15. The process according to claim 1 wherein the reaction product of the reaction is isolated by precipitation from an aqueous solution using a salt-forming acid followed by subsequent filtration.

16. The process according to claim 2 wherein the reaction product of the reaction is isolated by precipitation from an aqueous solution using a salt-forming acid followed by subsequent filtration.

17. The process according to claim 1 wherein the 5-amino-3-chloro-sulfonyl-1,2,4-triazole of the formula (II) is added in portions or continuously to the aniline of the formula (III).

18. The process according to claim 2 wherein the 5-amino-3-chloro-sulfonyl-1,2,4-triazole of the formula (II) is added in portions or continuously to the aniline of the formula(III).

* * * * *